(12) United States Patent
Ogata

(10) Patent No.: US 9,067,067 B2
(45) Date of Patent: Jun. 30, 2015

(54) LOW AMPERAGE CURRENT AND HEAT APPLICATOR

(71) Applicant: Kenneth K. Ogata, Honolulu, HI (US)

(72) Inventor: Kenneth K. Ogata, Honolulu, HI (US)

( * ) Notice: Subject to any disclaimer, the term of this patent is extended or adjusted under 35 U.S.C. 154(b) by 0 days.

(21) Appl. No.: 14/304,917

(22) Filed: Jun. 14, 2014

(65) Prior Publication Data
US 2015/0012052 A1    Jan. 8, 2015

Related U.S. Application Data

(60) Provisional application No. 61/957,487, filed on Jul. 5, 2013.

(51) Int. Cl.
| | | |
|---|---|---|
| *A61N 1/00* | (2006.01) | |
| *A61N 1/36* | (2006.01) | |
| *A61F 7/00* | (2006.01) | |
| *A61B 1/00* | (2006.01) | |
| *A61N 1/20* | (2006.01) | |
| *G06F 19/00* | (2011.01) | |

(52) U.S. Cl.
CPC ............ *A61N 1/36021* (2013.01); *A61F 7/007* (2013.01); *A61B 1/00* (2013.01); *A61B 1/00087* (2013.01); *A61N 1/205* (2013.01); *G06F 19/34* (2013.01); *A61F 2007/0071* (2013.01); *A61F 2007/0081* (2013.01); *A61F 2007/0093* (2013.01)

(58) Field of Classification Search
CPC ................. A61B 1/00; A61B 1/00087; A61F 2007/0071; A61F 2007/0081; A61F 2007/0093; A61F 7/007; A61N 1/205; A61N 1/36021; G06F 19/34
See application file for complete search history.

(56) References Cited

U.S. PATENT DOCUMENTS

| | | |
|---|---|---|
| 2,661,744 A | 12/1953 | Browner |
| 4,323,073 A | 4/1982 | Ferris |
| 4,374,517 A | 2/1983 | Hagiwara |
| 4,895,153 A | 1/1990 | Takeuchi et al. |
| 5,423,874 A | 6/1995 | D'Alerta |
| 6,408,211 B1 | 6/2002 | Powell |
| 7,860,571 B2 | 12/2010 | Pollock |
| 8,275,461 B2 | 9/2012 | Birkill et al. |
| 2007/0282400 A1* | 12/2007 | Gorham .................... 607/88 |

* cited by examiner

*Primary Examiner* — George Manuel
(74) *Attorney, Agent, or Firm* — Wade C. Yamazaki

(57) ABSTRACT

A combined heat and current applicator assembly including a heat applicator, a current applicator and a control unit. The heat applicator includes a housing, a heated tip and a cable for receiving electricity from the control unit. The current applicator includes a housing, a current tip, and a cable for receiving a low amperage alternating current from the control unit. The control unit allows a user to adjust a temperature of the heated tip and amperage of the current tip. The current applicator applies the low amperage current through the current tip to a specific, isolated afflicted area of a user or patient in order to strengthen the immune system and decrease local inflammation.

18 Claims, 12 Drawing Sheets

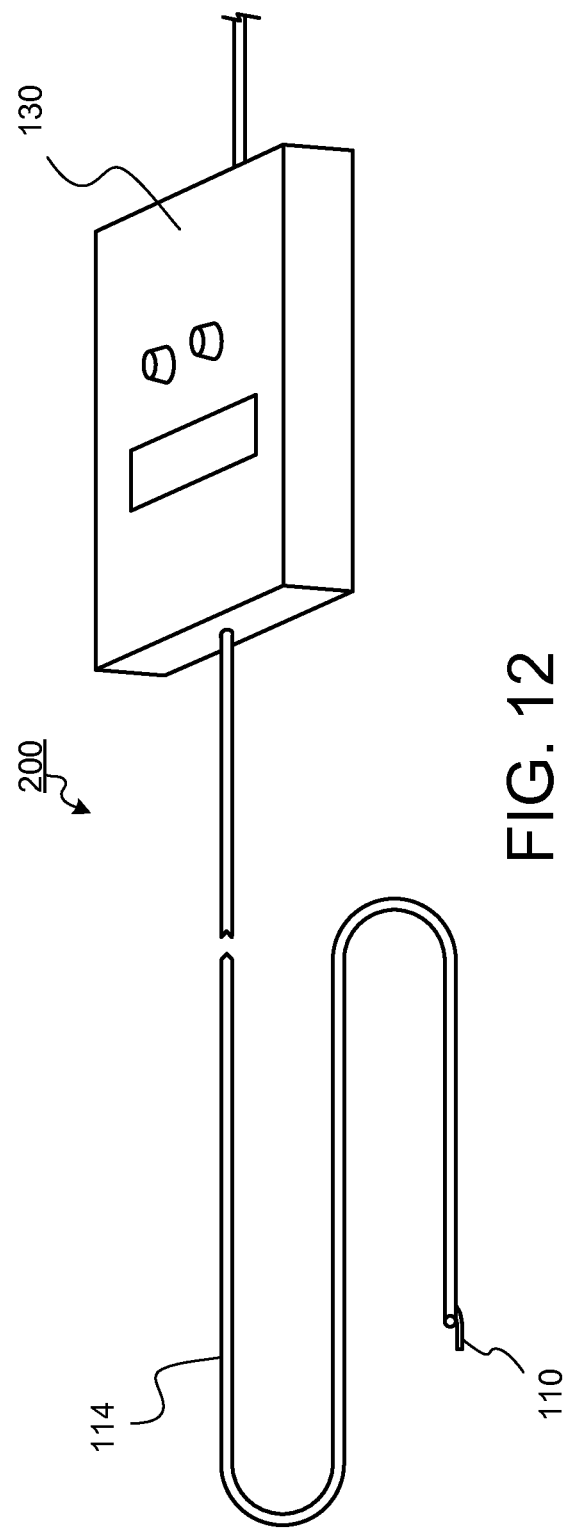

LOW AMPERAGE CURRENT AND HEAT APPLICATOR

CROSS REFERENCE TO RELATED APPLICATION

This application claims priority to U.S. Provisional Application Ser. No. 61/957,487 entitled "Kogata EMF/Heat Application Healing Process" filed Jul. 5, 2013; the contents of all of which are hereby incorporated by reference herein in their entirety into this disclosure.

TECHNICAL FIELD

The subject disclosure generally relates to heat and current applicators, and in particular, to healing various illnesses and relieving pain.

BACKGROUND

Many types of inflammation affect people in various ways on a day-to-day basis. Inflammation can cause pain and swelling, as well as lead to a number of diseases such as arthritis. For example, many people who suffer from arthritis have irritating and hampering joint pains and have difficulty with dexterous tasks. While many medications and surgeries exist to reduce inflammation and to reduce its symptoms, there is still a pressing need for a less invasive treatment option. Furthermore, while other devices exist to stimulate nerves for therapeutic purposes, none adequately target smaller afflicted areas such as those between fingers, toes or within body cavities.

BRIEF DESCRIPTION OF THE DRAWINGS

Various exemplary embodiments of this disclosure will be described in detail, wherein like reference numerals refer to identical or similar components or steps, with reference to the following figures, wherein:

FIG. 12 depicts another exemplary applicator assembly having an endoscope according to the subject disclosure.

DETAILED DESCRIPTION

Particular embodiments of the present invention will now be described in greater detail with reference to the figures.

Figure 1:
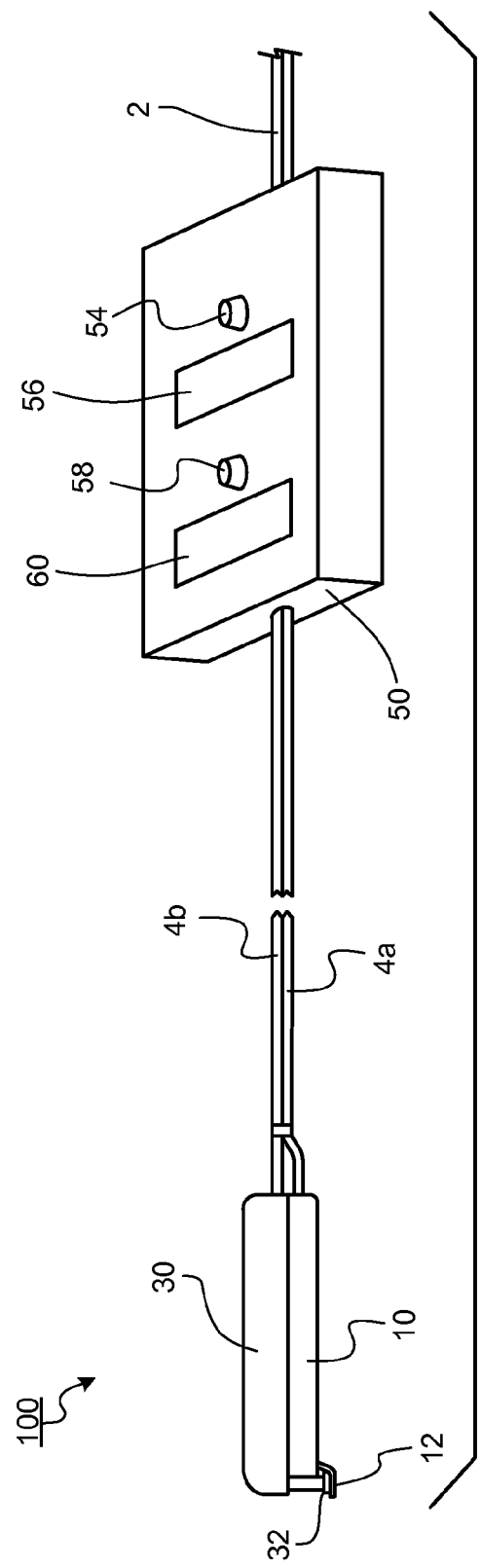
FIG. 1 illustrates an exemplary applicator assembly having a heat applicator, a current applicator and a control unit according to the subject disclosure.
Figure 2:
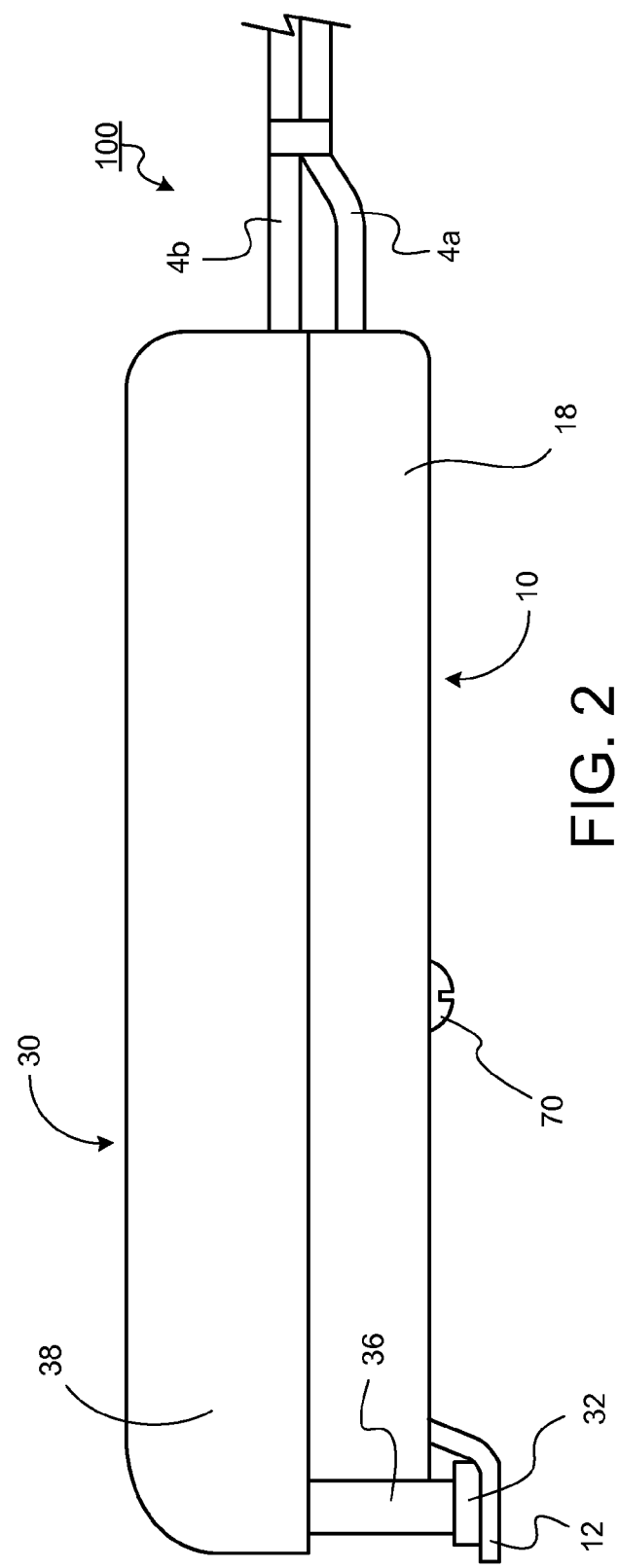
FIG. 2 shows an expanded side view of the heat and current applicator having a fastening device.

FIGS. 1-2 show an exemplary perspective view of an applicator assembly 100. The applicator assembly 100 comprises a current applicator 10, a heat applicator 30 and a control unit 50. The applicator assembly 100 is attached by a cable 2 to an outlet providing alternating current (AC) at any standard voltage and frequency. The current applicator includes a current tip 12 and housing 18. The heat applicator 30 includes a housing 38 and a heated tip 32 which provides a safe amount of heat to both the current tip 12 as well as a specific afflicted area of a patient or user. The user may be a human, animal, or any mammal.

Cable 4a provides a lower amperage alternating current to the current applicator 10 from the control unit 50. Cable 4b provides current to the heat applicator 30 from the control unit 50. Each cable 4a, 4b is coated with appropriate insulation to keep external sources from altering the current provided by each, as well as prevent each cable 4a, 4b from interfering with each other.

The current applicator 10 applies a low amperage current through the current tip 12 to the afflicted area in order to strengthen the immune system and decrease local inflammation. The current applicator 10 may provide a safe amount of current which will not interfere with the body's natural cardiac rhythms, which may be less than 0.03 amperes (30 milliamps), within a range of 0.002 amperes to 0.005 amperes (two to five milliamps), or any other suitable low amperage range.

Furthermore, the current tip 12 may be made of any conductive material such as silver, nickel, copper or any other suitable for transmitting low amperage current. The current tip 12 may be generally round and may have a diameter within a range of 0.125 inches to 0.5 inches, around about 0.25 inches. Additionally, the current tip 12 may take any suitable shape or size to allow for convenient application for hard to reach areas, like at finger joints and the like, or larger surface areas.

Unlike conventional devices, an aspect of the subject disclosure is to apply an electromotive force (EMF) treatment to a specific targeted area or region on a user, such as between finger joints or in body cavities. The small current tip 12 can easily reach all very small crevices and surface areas of a user's fingers, hands, toes, feet, ears, etc. The targeted surface area can be as small or focused as the dimensions and/or shape of the current tip 12. An advantage of targeting the specific afflicted area via the small current tip 12 is to directly apply the EMF treatment to the particular afflicted cells which are causing the discomfort or pain. In this way, the treatment is more effective and will reduce symptoms quicker with less relapse.

The current tip 12 may also be modular and removable from the housing 18 of the current applicator 10. The heated tip 32 may modular and removable from the housing 38 of the heat applicator 30 as well. Multiple configurations of the current tip 12 and heated tip 32, differentiating by size, shape, material, color, conductivity, or other factors, would allow for limitless customization for each user's particular needs, such as targeting in smaller areas, between fingers, or in body cavities.

Figure 3:
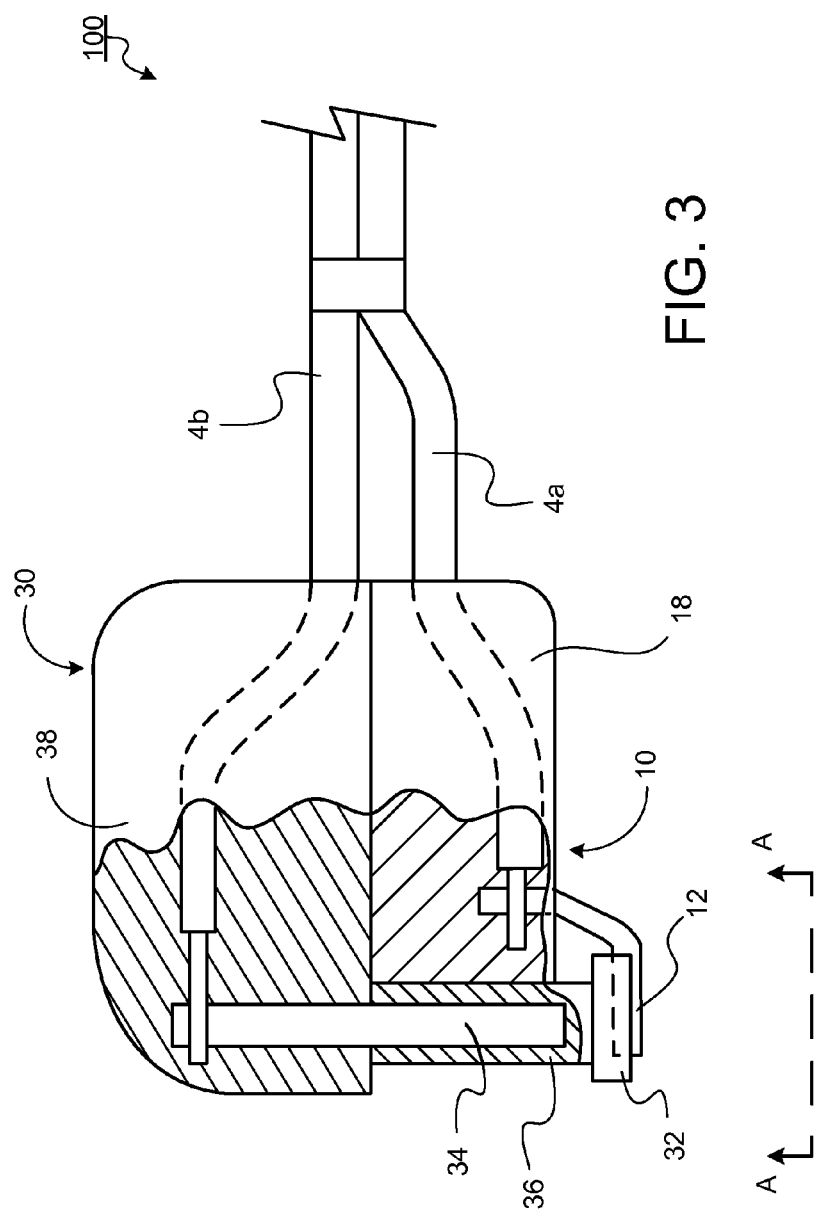
FIG. 3 depicts a partial cross section of the applicator assembly with the heat applicator tip configured to mate with the current applicator tip.

The heat applicator 30 generates heat to the heated tip 32. As depicted in FIG. 3, the heat applicator 30 may generate the heat by passing current from the cable 4b through a resistive heating element 34. The resistive heating element 34 may be a rod made of metal, such as copper, nichrome, cupronickel, or other suitable metal, or from a suitable ceramic, composite, or other combination which will produce heat when an electrical current is applied.

Figure 4:
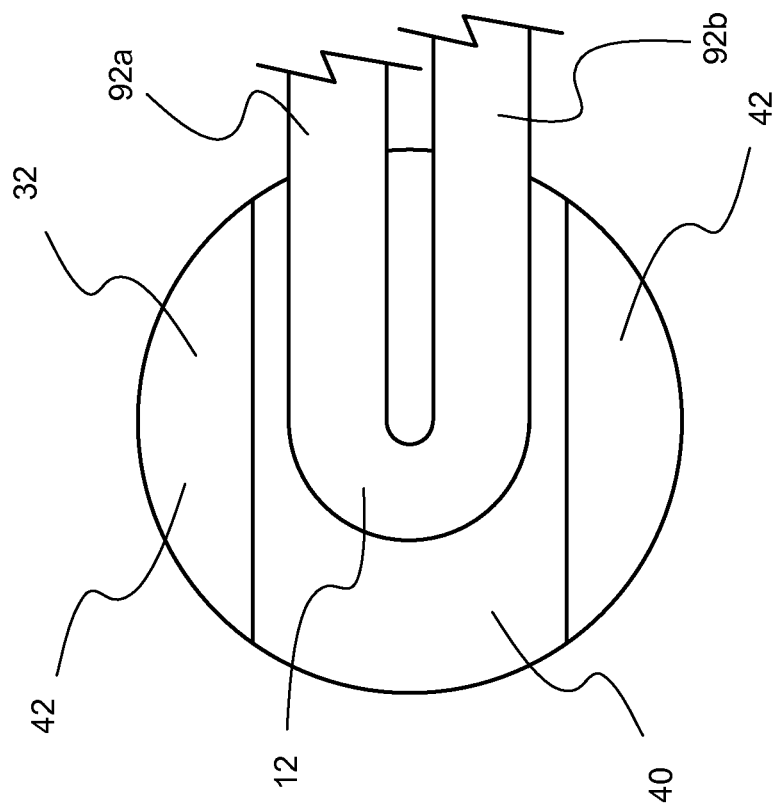
FIG. 4 illustrates a bottom view of the applicator tip from view A-A in FIG. 3.

The heated tip 32 may be generally round and may have a diameter less than a diameter of the current tip 12 (as shown in FIGS. 1 and 2) or may have a diameter greater than the diameter of the current tip 12 (as shown in FIGS. 3 and 4). The diameter of the heated tip 32 may be within a range of 0.0625 inches to 0.25 inches, around about 0.125 inches, or additionally may take any suitable shape or size.

FIG. 3 illustrates a partial cross-section of the applicator assembly 100. The heat applicator 30 may also include an insulated coating 36 which surrounds the resistive heating element 34. The insulated coating 36 protects the user from contacting the electrically charged resistive heating element 34 as well as conducts heat towards the heated tip 32. The insulated coating 36 may be made from a ceramic material, such as steatite, cordierite, alumina, zirconia, or any other suitable ceramic or insulating material to prevent contact with the resistive heating element 34.

The heated tip 32 is adapted to heat to a safe temperature to avoid burning or damaging the afflicted area, which may be less than 130 degrees Fahrenheit, or within a range of 90 degrees Fahrenheit to 120 degrees Fahrenheit. Increasing the temperature of the afflicted area will stimulate the production of white blood cells as well as help the afflicted area to be more receptive to the EMF treatment.

In use, a patient or physician may adjust the current applicator 10 to output a specified amount of current, subsequently contacting the specific afflicted area with the current tip 12. He or she may also adjust the heat applicator 30 to output a specified amount of heat while the current tip 12 is in contact with the afflicted area. This treatment may last anywhere from less than a minute to a few minutes, and may be repeated as needed until symptoms at the afflicted area significantly decrease or cease.

As shown in FIGS. 3-4, the heated tip 32 may also include a recessed portion 40 which is adapted to receive the current tip 12. Extruded portions 42 of the heated tip 32 may straddle either side of the current tip 12 to provide a more consistent heat distribution. An advantage of evenly distributing the heat across the current tip 12 is to increase the amount of heat being transferred to the afflicted area, rather than to the current tip 12 and then to the afflicted area.

Furthermore, while heating the current tip 12 will alter its resistance, the temperatures at which the heated tip 32 operates are low enough as to not significantly change the voltage or amperage of the current exiting the current tip 12. In addition, the current tip 12 receives the low amperage current from output wires 92a, 92b as shown, which will be discussed in more detail below.

As illustrated in FIG. 1, the control unit 50 may provide a heat switch 54, a heat display 56, a current switch 58 and current display 60. The heat switch 54 and current switch 58 may also be in the form of a knob, slide, rocker, touch screen, or other actuating system. The heat switch 54 allows the user to control the amount of current provided to the heat applicator 30, which will vary the temperature of a heated tip 32 as discussed in greater detail below.

Furthermore, the user will be able to adjust the amount of current traveling through the current tip 12 by adjusting the current switch 58. Both the current switch 58 and heat switch 54 may modulate the amount of current traveling through both cables 4a, 4b respectively using a variable resistor, transistor, or other suitable amplifier. Similarly, the user may turn off either or both the current applicator 10 and heat applicator 30 using either knob 54, 58 respectively.

Figure 5:
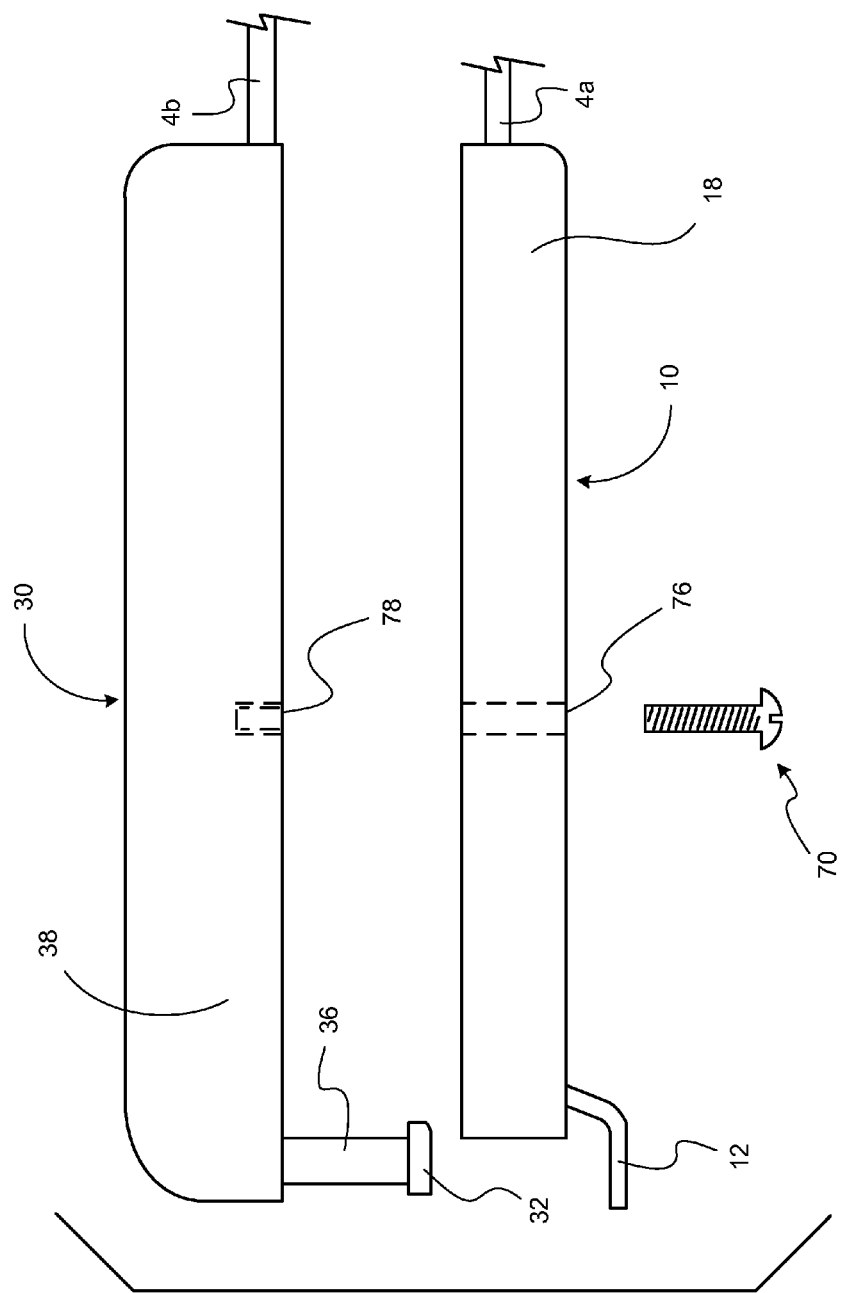
FIG. 5 shows an exploded view of the heat and current applicator.

As shown in FIG. 5, the current applicator 10 and heat applicator 30 may be used in combination or independently on the same or different targeted regions. In some use, heat cannot be applied and so the heat applicator 30 may be turned off. Using separate controls such as the switches 54, 58 may allow the user to use one applicator 10 or 30 with or without the other. The user may also completely and physically separate the current applicator 10 from the heat applicator 30. Furthermore, when used separately, the current applicator 10 may be applied to a first specific targeted region while the heat applicator 30 may be applied to a second specific targeted region.

FIG. 5 depicts the heat applicator 30 removed from the current applicator 10. The current applicator 10 and heat applicator 30 may be attached by a fastening device 70. Fastening device 70 may comprise a screw or bolt 72 which passes through an aperture 76 in the housing 18 of the current applicator 10 and is secured to a threaded hole 78 in the housing 38 of the heat applicator 30. The user may use the current applicator 10 in combination with the heat applicator 30, or may release the fastening device 70 to use them independently. The fastening device may also comprise snap-fasteners, magnets, hoop and loop mechanism (such as Velcro or the like), or interference fit.

Figure 6:
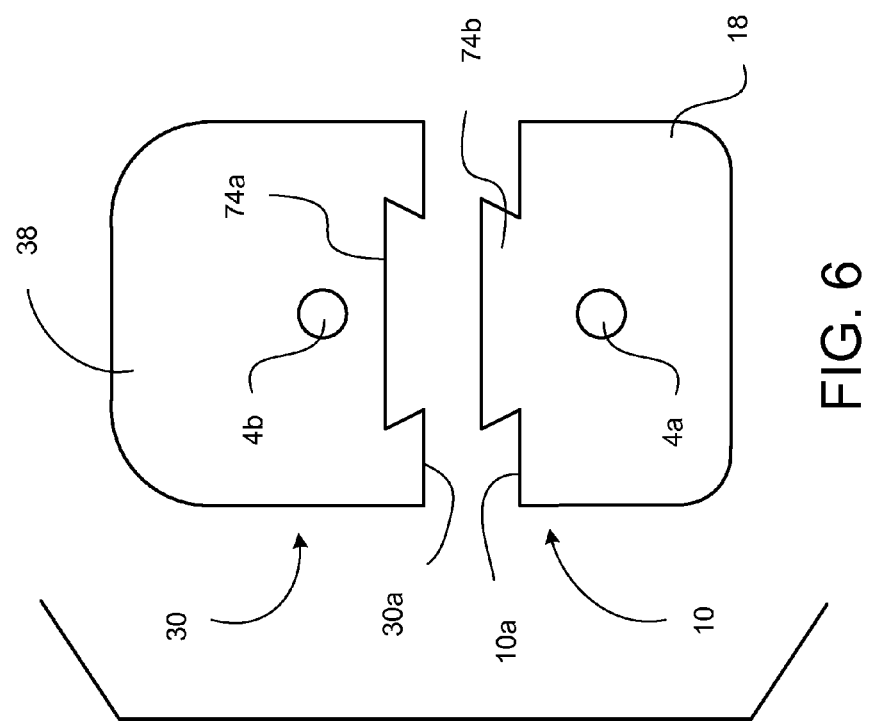
FIG. 6 depicts a rear view of the applicator assembly having the fastening device as a sliding fit fastening device from view B-B in FIG. 7.
Figure 7:
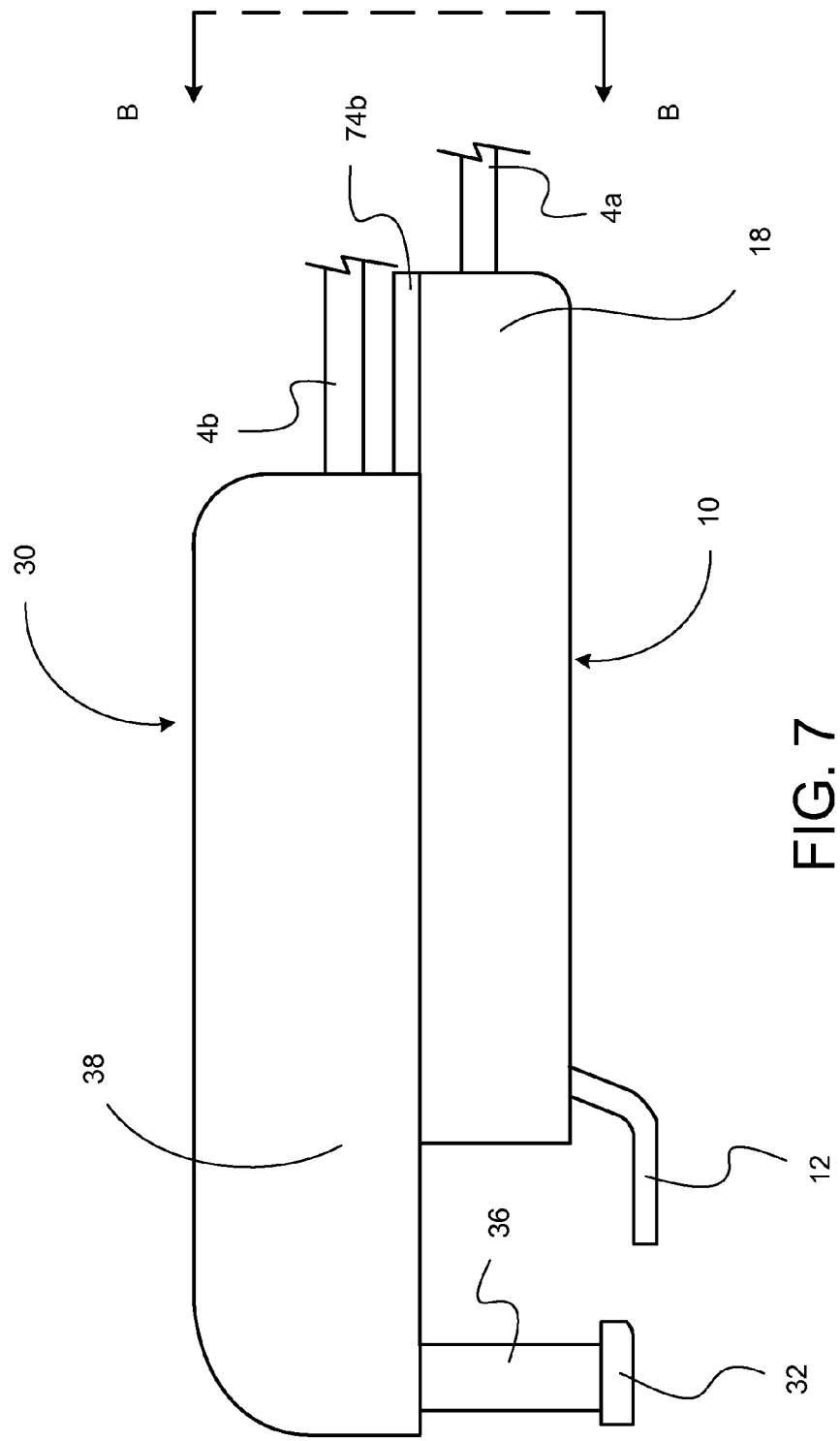
FIG. 7 illustrates a side view of the applicator assembly from FIG. 6 having the heat applicator partially detached from the current applicator.

FIGS. 6-7 illustrate the fastening device 70 as a sliding fit fastening device including at least one complementary groove 74a and protrusion 74b which matingly lock the heat applicator 30 and current applicator 10 together. While it is shown that the groove 74a is on a lower surface 30a and the protrusion 74b is on an upper surface 10a of the current applicator 10, it is to be understood that their construction may be reversed and/or located on any surface of either the heat applicator 30 or current applicator 10.

The configuration depicted in FIGS. 6-7 allow a user to easily slide and install the heat applicator 30 into the current applicator 10 by aligning the groove 74a and protrusion 74b for dual use. If either applicator 10, 30 is needed independently, the user or physician may simply break the friction fit between the two surfaces and separate the two applicators 10, 30.

Figure 8:
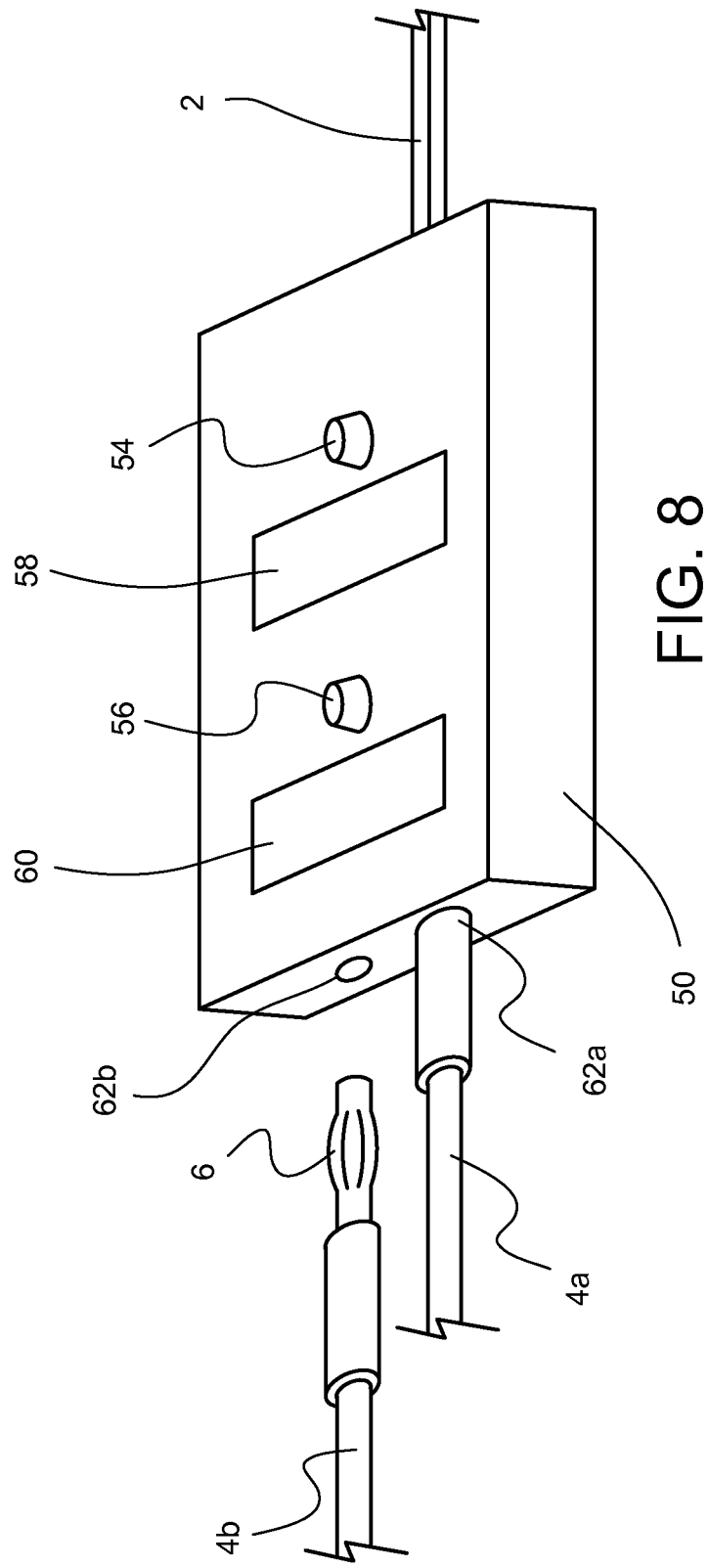
FIG. 8 shows the control unit having modular connectors for multiple current and heat applicators.

In order to facilitate using the current applicator 10 separately from the heat applicator 30, the control unit 50 may have separate outputs 62a, 62b for each applicator 10, 30 respectively, as depicted in FIG. 8. A connector 6 may be attached at an end of each wire 4a, 4b to facilitate removing or adding either applicator 10, 30. While the connector 6 is shown as a single pin connection, the connector may have multiple pins or electrodes as required by the applicator. For example, the current applicator 10 would have at least two pins that would connect with the output wires 92a, 92b and current tip 12. Furthermore, it is to be understood that any number of outputs and applicators may be used with the control unit 50, and appropriate switches may be introduced to control each of the applicators independently or in combination.

Figure 9:
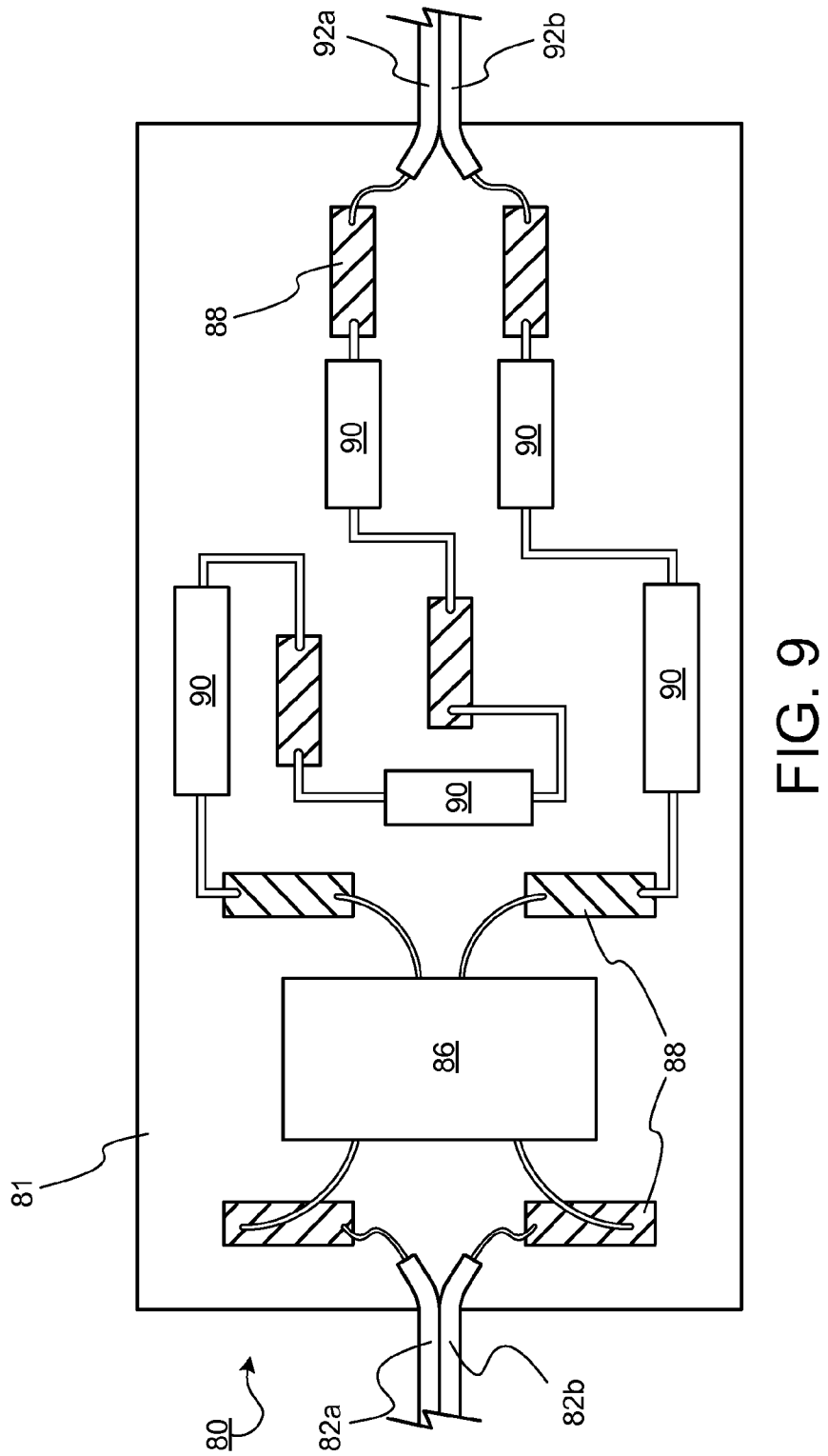
FIG. 9 depicts the internal structure of the current applicator.
Figure 10:
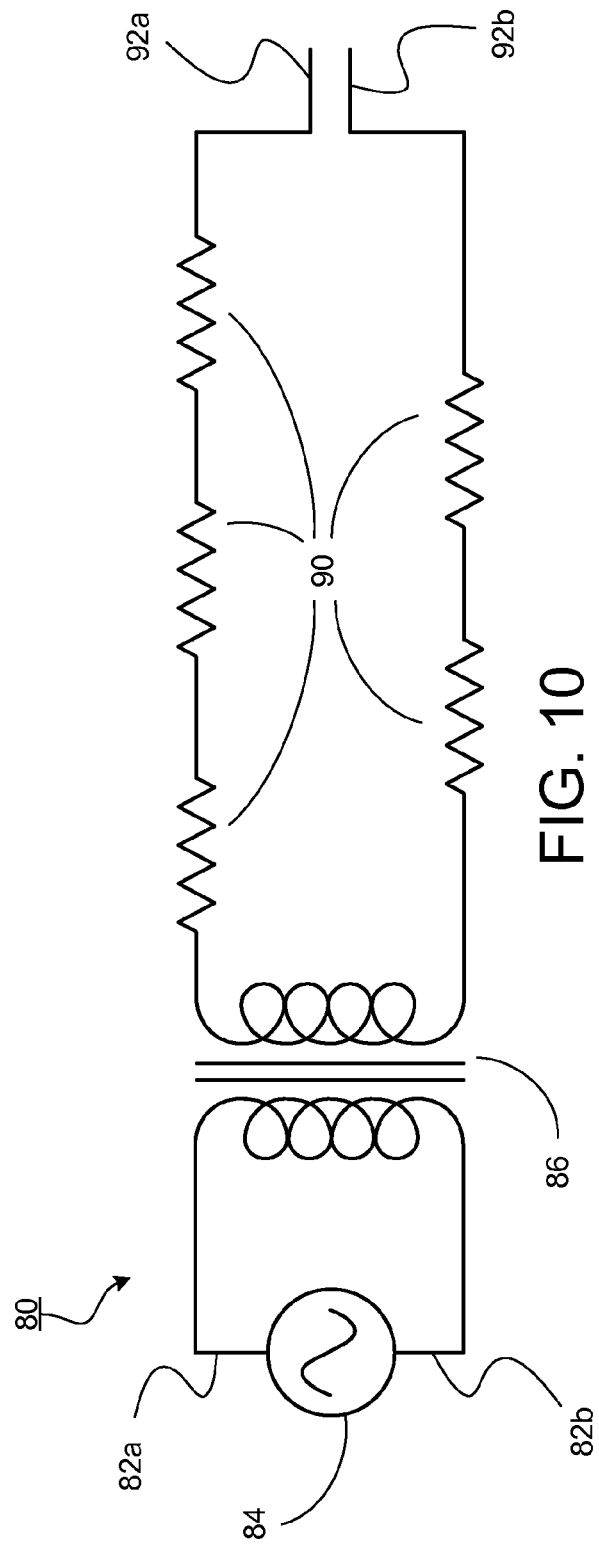
FIG. 10 illustrates an exemplary schematic circuit diagram for the current applicator.

FIGS. 9-10 show a schematic diagram of the current applicator circuit 80 having a circuit housing 81. In general, the current applicator circuit 80 converts an electrical signal from a standard outlet or power source into a low amperage electrical output capable of being applied to an afflicted area of a user's body. The schematic diagram of the current application circuit 80 shown in FIGS. 9-10 is shown for exemplary purposes. It is to be understood that other suitable configurations may be used in accordance with this subject disclosure. This particular schematic diagram illustrates an exemplary standard 120 V 60 Hz alternating current electrical signal into a 1.2 V alternating current electrical signal at approximately 0.003 ampere.

In general, an alternating current source 84 may supply electricity to input wires 82a, 82b. Additionally, the input signal may not only be from an outlet or alternating current source 84, but may be from a battery or other electronic device such as a computer or external controller. If the signal is received as a direct current signal, it may be converted into an alternating current signal by a configuration of diodes, power inverters, or other suitable methods for converting direct current into alternating current. Additionally, it may remain a direct current signal.

The current applicator circuit 80 may include at least one transformer 86 which receives electricity from the input wires 82a, 82b. The transformer 86 may significantly decrease the voltage of the incoming electrical signal and decrease the amperage. Here, the transformer 86 decreases the voltage from 120 V to 6 V. An advantage of decreasing the voltage of the incoming signal is to minimize the subsequent resistance required to decrease the output amperage.

The electric signal may then leave the transformer 86 and enter a series of resistors 90. The resistors 90 will decrease the voltage of the incoming electrical signal until it is the desired voltage and current at output wires 92a, 92b. The resistors 90 may take on any configuration or resistances suitable to transform the electrical signal into the desired amperage. As shown in FIG. 9, copper plates 88 may also be introduced to increase the conductivity of the electricity between the electrical components and ease the replacement of any components if repairs become subsequently necessary.

The control unit 50, as depicted in FIG. 1, may alter the electrical current in the current applicator circuit 80 as shown in FIG. 10 at any location between the alternating current source 84 and the output wires 92a, 92b by altering one of the resistors 90 such as by integrating a variable resistor. The current switch 58 may alter the resistance of one or more of the resistors 90 in order to vary the output voltage and amperage between output wires 92a, 92b. The output may also be controlled by the user through introducing a transistor (not shown) into the current applicator circuit 80, or other suitable method for increasing or decreasing the amperage and/or voltage within a circuit.

Figure 11:
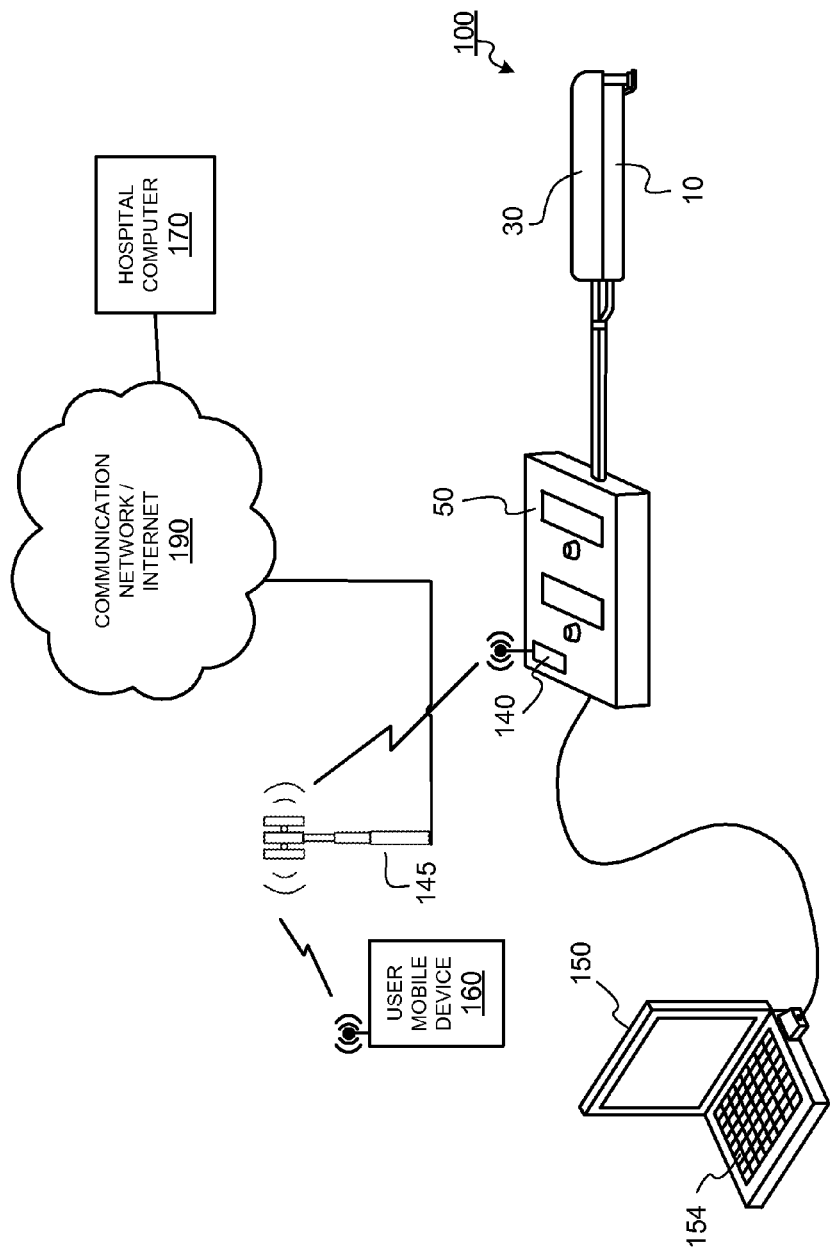
FIG. 11 shows the applicator assembly connected with a computer or like device.

FIG. 11 is a network diagram of the control unit 50 transmitting and receiving signals to and from a computer or like device 150, a user mobile device 160 and a remote computer 170, such as a hospital computer, via a communications network 190.

As shown, the control unit 50 is attached to the current applicator 10 and heat applicator 30, and includes a transceiver receiver 140 for wirelessly transmitting and receiving data to and from a mobile communications provider 145. The control unit 50 may also be connected wirelessly or by a cable to the computer 150.

The user may manually change the output heat or current level of the applicator assembly 100 by using the heat switch 54 or current switch 58, or instead enter in the desired heat or current level into an input device 154 attached to the computer 150. Alternatively, the user may input changes into the user mobile device 160, which may be a PDA, cell phone, touch pad, watch, or other mobile device. The user mobile device 160 would then transmit over the mobile communications provider 145 to the transceiver receiver 140 of the control unit 50. Alternatively, the user mobile device 160 may transmit information directly to the transceiver receiver 140 via Bluetooth, WiFi and/or other suitable wireless technology.

Furthermore, the user mobile device 160 may communicate with a remote doctor or physician using the hospital computer 170 over the communications network 190. The doctor may enter a prescribed treatment including various current and heat parameters into the hospital computer 170 and then transmit them directly to the user mobile device 160, transceiver receiver 140, or computer 150. The doctor may also transmit treatment instructions by video, audio, text or other data or the like.

In addition, the control unit 50 may receive power to supply to the applicators 10, 30 directly from the computer 150 as shown, or from an outlet as previously discussed. Furthermore, the computer 150 may wirelessly connect to the control unit 50, allowing the user or physician to monitor and/or control the applicators 10, 30 from the computer 150 but easily manipulate and apply the applicators 10, 30 to any potential afflicted areas.

FIG. 12 depicts another exemplary applicator assembly 200 wherein a current applicator 110 is attached to an endoscope 130 such that the low amperage treatment may be made to body cavities such as those found in the gastrointestinal track, respiratory track, urinary track, or other internal body cavities without the need for surgery.

The applicator assembly 200 may also include an eyepiece or videoscope with a light delivery system to transmit an image showing the location of the current applicator 110 in relation to the internal afflicted area. Furthermore, the current wires 114 may be thin and braided for flexibility, as well as include waterproof or moisture resistant components to shield the electronics therein.

The illustrations and examples provided herein are for explanatory purposes and are not intended to limit the scope of the appended claims. It will be recognized by those skilled in the art that changes or modifications may be made to the above described embodiment without departing from the broad inventive concepts of the invention. It is understood therefore that the invention is not limited to the particular embodiment which is described, but is intended to cover all modifications and changes within the scope and spirit of the invention.

What is claimed is:

1. A combined heat and current applicator assembly, comprising:
    a heat applicator having a first housing and a heated tip;
    a current applicator having a second housing and a current tip; and
    a control unit attached to both the heat applicator and the current applicator, the control unit including at least one heat switch to adjust a temperature of the heated tip and at lest one current switch to adjust an amperage of the current tip, the control unit including at least one transformer and at least one resistor,
    wherein the control unit receives an input electrical signal at a first voltage and a first amperage and transforms that signal into an output electrical signal with a lower second voltage and a lower second amperage,
    wherein the current tip conducts a low amperage electrical signal adapted to be applied to a surface of a user.

2. The combined heat and current applicator assembly as recited in claim 1, wherein the low amperage electrical signal is an alternating current electrical signal.

3. The combined heat and current applicator assembly as recited in claim 2, wherein the alternating current electrical signal is less than about 30 amperes.

4. The combined heat and current applicator assembly as recited in claim 1, wherein the heat applicator further comprises a resistive heating element which generates and provides heat to the heated tip, and an insulated coating which surrounds the resistive heating element.

5. The combined heat and current applicator assembly as recited in claim 1, wherein the current tip is adapted to be applied to a specific targeted region of the user in a space defined by a dimension of the current tip.

6. The combined heat and current applicator assembly as recited in claim 1, wherein the heated tip includes a recessed portion adapted to receive the current tip.

7. The combined heat and current applicator assembly as recited in claim 1, further comprising a fastener attaching the heat applicator to the current applicator.

8. The combined heat and current applicator assembly as recited in claim 7, wherein the fastener includes a threaded screw and at least one threaded aperture located on a surface of the heat applicator or the current applicator.

9. The combined heat and current applicator assembly as recited in claim 7, wherein the fastener includes at least one complementary protrusion and receiving groove, the protrusion and receiving groove being located on a surface of one of either the heat or current applicator respectively.

10. The combined heat and current applicator assembly as recited in claim 1, wherein the current tip is modular and removable from the current applicator.

11. The combined heat and current applicator assembly as recited in claim 1, wherein the current tip is attached to an endoscope.

12. A pain relieving device, comprising:
a heat application device having a heated applicator and a first electrical input;
a current application device having a current applicator and a second electrical input; and
a controller connected to the first and second electrical inputs for adjusting a temperature of the heated applicator and an amperage of the current applicator, the controller having at least one current switch to adjust the amperage of the current applicator and at least one heat switch to adjust the temperature of the heated applicator, wherein the controller further comprises at least one transformer and at least one resistor to transform the second electrical input at a first voltage and a first amperage into an output electrical signal with a lower second voltage and a lower second amperage,
wherein the current applicator conducts a low amperage alternating current and the heat applicator applies heat to the current applicator.

13. The pain relieving device as recited in claim 12, further comprising a fastening device for removably attaching the heat application device to the current application device.

14. The pain relieving device as recited in claim 12, wherein the current applicator is adapted to be applied to a targeted afflicted area defined by a dimension of the current applicator.

15. A method of relieving pain from inflammation, comprising the steps:
providing a circuit inside a housing including a current applicator, a heat applicator and input source;
providing a control unit connectable to the circuit having a current switch, a heat switch, a transformer and at least one resistor;
transforming the input source having a first voltage and a first amperage into an output electrical signal having a lower second voltage and lower second amperage;
varying a low amperage current in the current applicator with the current switch of control unit and varying a temperature of the heat applicator with the heat switch of the control unit; and
applying the current applicator to an afflicted area of a user.

16. The method as recited in claim 15, further comprising:
heating the current applicator and afflicted area with the heat applicator.

17. The method as recited in claim 15, wherein the current applicator is applied to an isolated, targeted area of the user defined by a dimension of the current applicator.

18. The method as recited in claim 15, wherein the current applicator is attached to an end of an endoscope attached to the housing of the circuit.

\* \* \* \* \*